US00PP21499P2

(12) United States Plant Patent
Hoekstra-Arisz

(10) Patent No.: US PP21,499 P2
(45) Date of Patent: Nov. 16, 2010

(54) ***AGAPANTHUS* PLANT NAMED 'SOFIE'**

(50) Latin Name: ***Agapanthus* hybrid**
Varietal Denomination: Sofie

(76) Inventor: Catharina Marie Hoekstra-Arisz, Creutzberglaan 10, Beverwijk (NL) 1943

( * ) Notice: Subject to any disclaimer, the term of this patent is extended or adjusted under 35 U.S.C. 154(b) by 0 days.

(21) Appl. No.: 12/459,823

(22) Filed: Jul. 7, 2009

(51) Int. Cl.
*A01H 5/00* (2006.01)

(52) U.S. Cl. ..... Plt./398

(58) Field of Classification Search ..... Plt./398
See application file for complete search history.

*Primary Examiner*—June Hwu

(57) ABSTRACT

A new and distinct *Agapanthus* hybrid cultivar named 'SOFIE' is disclosed, characterized by upright leaf growth, umbels with a high quantity of individual flowers of a dark blue flower color. The new variety is an *Agapanthus* hybrid, suitable for outdoor landscape and decorative cut flower stem use.

1 Drawing Sheet

Figure 1:
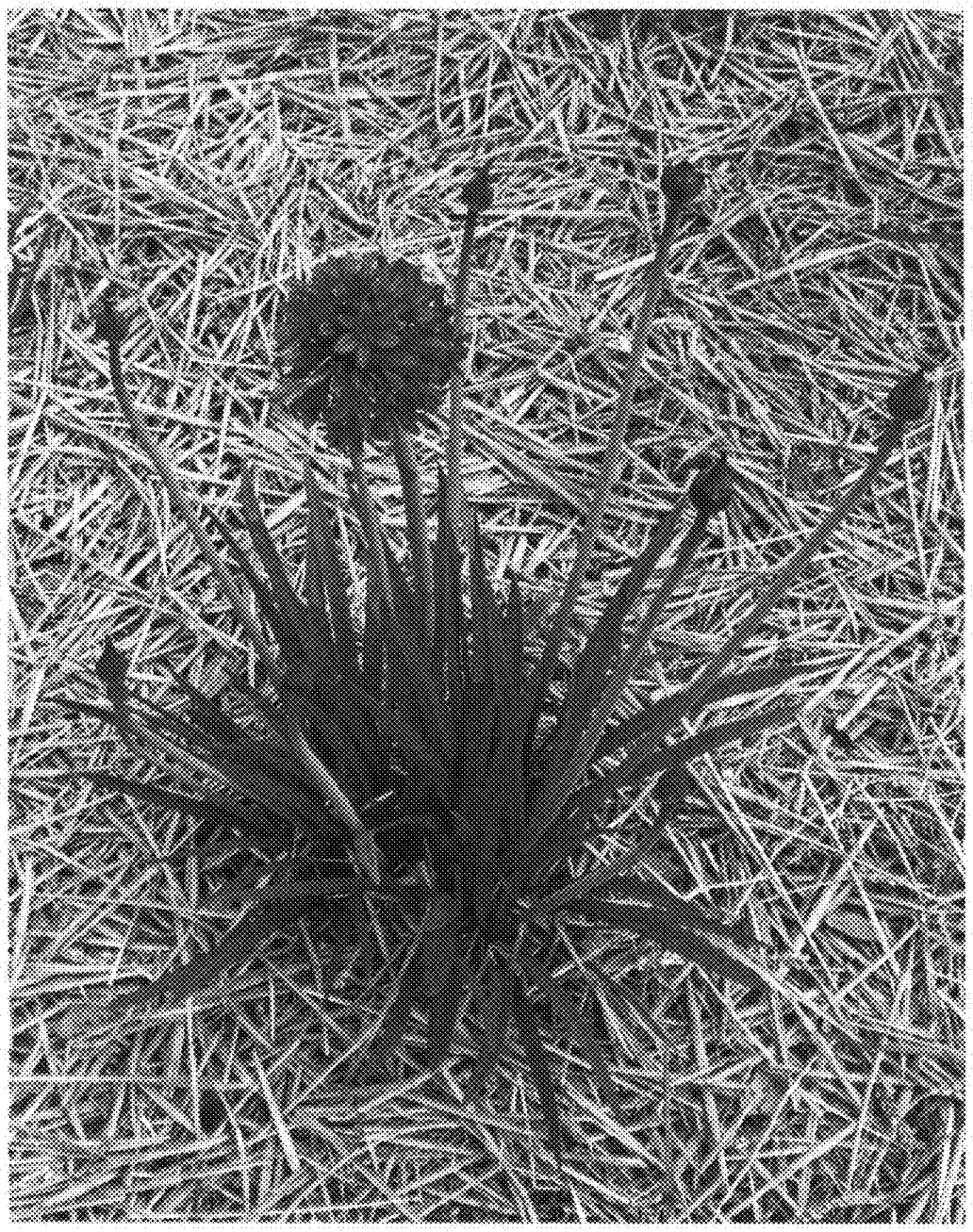

Latin name of the genus and species: *Agapanthus* hybrid.
Variety denomination: 'SOFIE'.

BACKGROUND OF THE INVENTION

The new cultivar is a chance seedling selection by the inventor, Catharina Maria Hoekstra-Arisz, a citizen of the Netherlands. The new variety was discovered at a commercial nursery in Beverwijk, The Netherlands, during the Summer of 2003, by the inventor growing in the ground among a field of mixed commercial varieties of *Agapanthus*. The parent varieties are unknown.

Asexual reproduction of the new cultivar 'SOFIE' by vegetative divisions was first performed in September 2006, at a commercial nursery in Beverwijk, The Netherlands and has shown that the unique features of this cultivar are stable and reproduced true to type in successive generations.

SUMMARY OF THE INVENTION

The cultivar 'SOFIE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SOFIE' These characteristics in combination distinguish 'SOFIE' as a new and distinct *Agapanthus* cultivar:

1. Upright leaf growth.
2. Umbels with a high quantity of individual flowers.
3. Dark blue flower color.
4. Compact plant habit.

COMMERCIAL COMPARISION

Plants of the new cultivar 'SOFIE' are similar to plants of the unpatented variety, *Agapanthus* hybrid 'Intermedia' in most horticultural characteristics, however, plants of the new cultivar have lighter colored scapes, foliage with a more upright habit, and more individual flowers per umbel. Additionally, the new variety produces flowers of a dark blue color, rather than the dark purple of 'Intermedia'.

Plants of the new cultivar 'SOFIE' are similar to plants of the unpatented variety, *Agapanthus* hybrid 'Johanna' in most horticultural characteristics, however, plants of the new cultivar have a shorter, more compact umbel, longer lasting individual flowers, and more individual flowers per umbel. Additionally, the new variety produces flowers of a dark blue color, rather than the light blue of 'Johanna'.

BRIEF DESCRIPTION OF THE PHOTOGRAPH

The accompanying photograph in FIG. 1 illustrates in full color typical plants of 'SOFIE' grown outdoors in Beverwijk, The Netherlands. The plant is approximately 2 years old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'SOFIE' plants grown outdoors in Beverwijk, The Netherlands. The growing temperature ranged from approximately 1° to 12° C. at night and 10° to 25° C. during the day. Plants were described in October of 2008. Measurements and numerical values represent averages of typical flowering types. No chemical or photoperiodic treatments were given.
Botanical classification: *Agapanthus* hybrid 'SOFIE'.

PROPAGATION

Time to initiate roots: About 21 days at approximately 22° C.
Root description: Moderately dense, fleshy and slightly fibrous, color near RHS Greyed-White 156C.
Propagation method: Vegetative divisions or tissue culture. The plant described was propagated by tissue culture.

PLANT

Growth habit: Semi-hardy herbaceous perennial forming multiple basal rosettes.

Age of plant described: Approximately 36 months from a tissue culture plantlet.
Container size: Field grown plant.
Height: Approximately 29.9 cm to top of highest leaf. Approximately 66.4 cm to top of highest inflorescence.
Plant spread: Approximately 50.6 cm.
Growth rate: Inflorescences grow approximately 10 cm per month.
Branching characteristics: Non-branching, forms basal clumps.

FOLIAGE

Leaf:
*Arrangement.*—Basal rosette.
*Average length.*—Approximately 27.7 cm.
*Average width.*—Approximately 2.3 cm.
*Shape of blade.*—Linear.
*Apex.*—Acute.
*Base.*—Broad cuneate.
*Margin.*—Entire.
*Texture of top surface.*—Smooth, moderately glossy.
*Texture of bottom surface.*—Smooth, slightly glossy.
*Quantity of leaves per plant.*—Approximately 70.
*Color.*—Young foliage upper side: Near RHS Green 143A. Young foliage under side: Near RHS Green 143B. Mature foliage upper side: Near RHS Green 141A. Mature foliage under side: Near RHS Green 143A.
*Venation.*—Type: Linear. Venation color upper side: Near RHS Green N137B. Venation color under side: Near RHS Green 144A.

FLOWER

Natural flowering season: Summer.
Inflorescence type and habit: Terminal umbel, growing on a scape directly from the base of the plant.
Flower opening: Lowest flowers in the umbel open first, followed by consecutively higher flowers. At height of flowering period approximately 60% of the flowers are open at once.
Flower longevity on plant: Approximately 10 days, for individual flowers.
Quantity of flowers: Approximately 150 flowers per inflorescence
Umbel inflorescence size:
*Height.*—Approximately 9 cm.
*Width.*—Approximately 11 cm.
Corolla:
*Arrangement.*—Rotate.
*Size.*—Length: Approximately 2.6 cm. Width: Approximately 3.2 cm at widest point. Lobe Length: Approximately 1.8 cm. Lobe Width: 0.75 cm.
*Margin.*—Entire.
*Shape.*—Obovate.
*Apex.*—Bluntly acute.
*Texture.*—Smooth, slightly glossy, slightly velvety.
Color:
*Tepals.*—When opening: Outer surface: Near RHS Violet-Blue N89C with a central band of near RHS Violet-Blue 93A. Inner surface: In between near RHS Violet-Blue N89D and Violet-Blue 94A with a central band of near RHS Violet-Blue N89B.
*Fully opened.*—Outer surface: Near RHS Violet-Blue N89D with a central band of near RHS Violet-Blue N89B. Inner surface: In between near RHS Violet-Blue N89D and Violet-Blue 93B with a central band of near RHS Violet-Blue N89B. Color changes when aging: Near RHS Violet-Blue 93C to near Violet-Blue 94A.
Bud:
*Shape.*—Oblanceolate.
*Length.*—Approximately 2.0 cm.
*Diameter.*—Approximately 0.6 cm.
*Color.*—Near RHS Violet-Blue N89B.
Sepals: Not Present.
Pedicels:
*Length.*—Approximately 1.5 cm.
*Width.*—Approximately 0.1 cm.
*Aspect.*—Slightly drooping to upright (average angle from approximately 120° to 0° to −120° (0° =straight upright).
*Color.*—Near RHS Yellow-Green 144B.
Scape:
*Length.*—Approximately 80 cm.
*Width.*—Oval in cross-section, approximate width at widest: 1.2 cm, approximate width at narrowest: 1.0 cm.
*Angle.*—Straight upright, growing from base of plant.
*Strength.*—Very strong.
*Color.*—Near RHS Yellow-Green 144A.
Fragrance: Faint, typical Agapanthus-fragrance.

REPRODUCTIVE ORGANS

Stamens:
*Number.*—Average 6.
*Filament length.*—Approximately 1.4 cm.
*Filament color.*—Near RHS Violet-Blue 90B, lighter towards the base; near RHS Violet-Blue 91A.
*Anther length.*—0.15 cm.
*Anther color.*—Near RHS Violet-Blue 93C.
*Anther shape.*—Oblong.
*Pollen.*—Moderate to low, color near RHS Violet-Blue 93C.
Pistil:
*Number.*—1.
*Length.*—Approximately 1.3 cm.
*Style color.*—Near RHS Violet-Blue 90B.
*Stigma.*—Shape: Flattened club-shaped. Color: Near RHS Violet-Blue 91C. Ovary color: Near RHS Yellow-Green 150B.

OTHER CHARACTERISTICS

Seeds and fruits: No fruits detected to date.
Disease resistance: Neither resistance nor susceptibility to diseases or pests has been observed in this variety.
Drought tolerance and cold tolerance: Tolerates high temperatures to at least 35° C. Tolerates low temperatures to at least −5° C. While specific drought tolerance has not been observed, once plants are established moderate water is necessary to maintain plants.

What is claimed is:

1. A new and distinct cultivar of *Agapanthus* plant named 'SOFIE' as herein illustrated and described.

* * * * *